United States Patent [19]

L'Italien

[11] 4,372,960

[45] Feb. 8, 1983

[54] QUATERNARY DERIVATIVES OF N-(SUBSTITUTED-AMINOALKYL)-2-OXO-1-PYRROLIDINE-ACETAMIDES AS COGNITION ACTIVATORS

[75] Inventor: Yvon J. L'Italien, Plymouth, Mich.

[73] Assignee: Warner-Lambert Company, Morris Plains, N.J.

[21] Appl. No.: 215,959

[22] Filed: Dec. 12, 1980

[51] Int. Cl.$^3$ .................. A61K 31/40; A61K 31/445; C07D 207/27; C07D 401/12
[52] U.S. Cl. .............................. 424/267; 424/248.54; 424/250; 424/274; 544/141; 544/372; 546/208; 548/523; 548/543
[58] Field of Search ...................... 260/326.43, 326.25; 544/141, 372; 546/208; 424/248.54, 250, 267, 274

[56] References Cited

U.S. PATENT DOCUMENTS 3,509,171 4/1970 Welstead et al. .................. 544/141
4,145,347 3/1979 L'Italien et al. ............... 260/326.43

*Primary Examiner*—Alton D. Rollins
*Attorney, Agent, or Firm*—Walter Patton

[57] ABSTRACT

Quaternary derivatives of N-(substituted-aminoalkyl)-2-oxo-1-pyrrolidineacetamide are disclosed. These compounds are useful for treating senility, for enhancing memory and for reversing amnesia.

12 Claims, No Drawings

QUATERNARY DERIVATIVES OF N-(SUBSTITUTED-AMINOALKYL)-2-OXO-1-PYRROLIDINE-ACETAMIDES AS COGNITION ACTIVATORS

BACKGROUND OF THE INVENTION

Because of increased lifespan, the population of geriatric patients is ever increasing. This type patient possesses certain unique disabilities, one of which is senility. The present invention provides new compounds which are potentially useful for the treatment of senility.

SUMMARY OF THE INVENTION

The invention sought to be patented in its generic chemical compositions aspect is a compound having the structural formula:

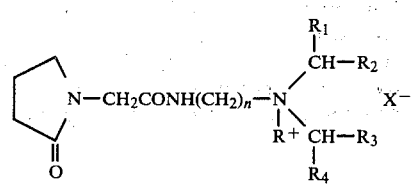

wherein R is alkyl of from 1 to 3 carbon atoms, $R_1$ and $R_4$ may be the same or different and are hydrogen or methyl; $R_2$ and $R_3$ may be the same or different and are hydrogen, alkyl of from 1 to 3 carbon atoms or when taken together can complete a pyrrolidine, piperidine, morpholine or piperazine ring; n is an integer of from 1 to 3; $X^-$ is a pharmaceutically acceptable anion; with the proviso that when R is n-$C_3H_7$, n is 2 and $X^-$ is I; $R_1$-$R_4$ may not all be hydrogen.

The invention sought to be patented in its chemical process aspect is a process for preparing a compound having the structural formula I

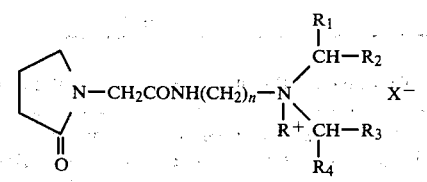

wherein R is alkyl of from 1 to 3 carbon atoms, $R_1$ and $R_4$ may be the same or different and are hydrogen or methyl; $R_2$ and $R_3$ may be the same or different and are hydrogen, alkyl of from 1 to 3 carbon atoms or when taken together can complete a pyrrolidine, piperidine, morpholine or piperazine ring; n is an integer of from 1 to 3; $X^-$ is a pharmaceutically acceptable anion; with the proviso that when R is n-$C_3H_7$, n is 2 and $X^-$ is I; $R_1$-$R_4$ may not all be hydrogen; which comprises (a) contacting a tertiary base having the structural formula

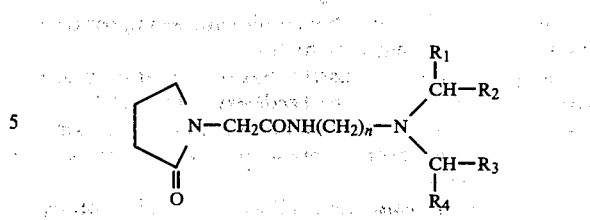

with a compound of the formula RX wherein R-$R_4$, n and X are defined above; and (b) isolating the product.

The invention sought to be patented in its pharmaceutical composition aspect is a composition useful for the treatment of senility, enhancing memory or reversing amnesia in a mammal which comprises an effective amount of a compound defined by structural formula I, or mixtures thereof; in combination with a pharmaceutically acceptable carrier.

The invention sought to be patented in its pharmaceutical method aspect is a method for treating senility, for enhancing memory, or for reversing amnesia in a mammal which comprises administering to a mammal in need thereof an effective amount of the pharmaceutical composition as defined above.

DESCRIPTION OF THE PREFERRED EMBODIMENTS

The quaternary salts having structural formula I may be prepared from the corresponding tertiary bases by treatment with a compound having the structural formula R—X. Both R and X are defined above. In addition, a tertiary base which already contains the group R may be treated with a compound having the structural formula $R_1R_2$CHX or $R_3R_4$CHX wherein $R_1$-$R_4$ and X are defined above. Those skilled in the art will recognize that the order of addition of the various alkyl groups to form the quaternary salts will not generally be critical to the practice of the invention. In the circumstance when $R_2$ and $R_3$ when taken together complete a heterocyclic ring the R group will most conveniently be added last.

The necessary tertiary bases may be prepared by methods disclosed in U.S. Pat. No. 4,145,347. This patent is incorporated by reference herein.

The preferred method for preparing the quaternary salts defined by structural formula I is by contacting the tertiary free base with an alkyl iodide, RI in a polar solvent. Examples of suitable polar solvents are ethyl alcohol and acetonitrile. The iodide anion may subsequently be exchanged for another pharmaceutically acceptable anion, such as the chloride anion, by methods known to those skilled in the art. For example, by use of an ion exchange resin.

The alkyl groups contemplated by the invention are methyl, ethyl, propyl and i-propyl. The pharmaceutically acceptable anions contemplated by the invention are all non-toxic anions known to those skilled in the art. Examples of such anions are $OH^-$, $Cl^-$, $Br^-$, $I^-$, $NO_3^-$, $R'SO_4^-$ wherein R' is alkyl of from 1 to 3 carbon atoms and the like. The chlorine anion is preferred.

The quarternary salts of the invention are new chemical compounds of value as pharmacological agents. More specifically, they are cognition activators which are potentially useful for treating patients suffering from senility, lost or impaired memory or amnesia. In addition, the alerting and attention focusing quality of these compounds would make them useful in treating patients having certain learning disabilities.

The pharmaceutical usefulness of the quaternary bases of the invention may be determined by the test described below. This test is designed to show the compound's ability to reverse amnesia produced by an electroconvulsive shock.

One hundred male mice (Carworth, CF-1 strain, 19-21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 milliamps delivered for 1 sec through the ears. Immediately thereafter, the mice are returned to the holding cage.

Two hours after the convulsive treatment, the mice are treated orally with the chemical being assessed. Usually three doses of the chemical will be tested at a time.

One hour after the drug treatment, the mice are tested for memory of the painful foot shock received within the shelf-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60 second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| GROUP | | TREATMENTS |
|---|---|---|
| (1) | Ceiling Control Group: | Placebo |
| (2) | Base Line Control Group: | Electroconvulsive shock Placebo |
| (3) | 1st Drug Dose Group: | Electroconvulsive shock Test Compound |
| (4) | 2nd Drug Dose Group: | Electroconvulsive shock Test Compound |
| (5) | 3rd Drug Dose Group | Electroconvulsive shock Test Compound |

The percent of amnesia reversal is determined as follows for each drug group:

Percent amnesia reversal =

$$\frac{\text{Drug group} - \text{Base Line Control Group}}{\text{Ceiling control group} - \text{Base line control group}} \times 100$$

The following criteria is used in interpreting the percent of amnesia reversal scores:

Forty percent or more (active); 25 to 39 percent (borderline); and 0 to 29 percent (inactive). The following table reports the results for certain compounds of the invention.

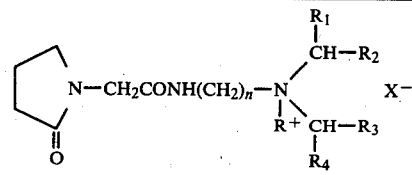

| | | | | | | | % Amnesia Reversal at Indicated Dose, Mg/kg in Mice P.O. | | | | | | | | |
|---|---|---|---|---|---|---|---|---|---|---|---|---|---|---|---|
| R | $R_1$ | $R_4$ | $R_2$ | $R_3$ | $X^-$ | n | .63 | 1.25 | 2.5 | 5 | 10 | 20 | 40 | 80 | 160 |
| $CH_3$ | $CH_3$ | $CH_3$ | $CH_3$ | $CH_3$ | I | 2 | 33 | 33 | 50 | 87 | | 87 | | 100 | |
| $CH_3$ | $CH_3$ | $CH_3$ | $CH_3$ | $CH_3$ | Cl | 2 | 64 | 45 | 64 | 100 | | 83 | | 67 | |
| $CH_3$ | H | H | H | H | I | 2 | | | | 29 | 77 | 71 | 69 | 64 | 62 |
| $n\text{-}C_3H_7$ | H | H | H | H | I | 2 | | | | 0 | | 11 | | 11 | |
| $CH_3$ | H | H | $-(CH_2)_3-$ | | I | 2 | | | | 55 | 43 | 55 | 71 | 91 | 50 |
| $C_2H_5$ | H | H | $-(CH_2)_3-$ | | I | 2 | | | | 50 | | 100 | | 50 | |
| $i\text{-}C_3H_7$ | H | H | H | H | I | 2 | | | | 60 | | 13 | | 50 | |
| $CH_3$ | $CH_3$ | $CH_3$ | $-(CH_2)_3-$ | | I | 2 | | | | 75 | | 47 | | 50 | |
| $CH_3$ | H | H | H | H | Cl | 3 | | | | 36 | | 63 | | 18 | |

The compounds of the invention can exist in both solvated as well as unsolvated forms, including hydrated forms. In general, the solvated forms, with pharmaceutically acceptable solvents such as water, ethanol and the like are equivalent to the unsolvated forms for purposes of the invention.

The compounds of the invention can be prepared and administered in a wide variety of oral and parenteral dosage forms. It will be clear to those skilled in the art that the following dosage forms may comprise as the active component, either a compound of formula I, or a mixture of such compounds.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form.

The quantity of active compound in a unit dose of preparation may be varied or adjusted from 1 mg to 100 mg according to the particular application and the potency of the active ingredient.

In therapeutic use as agents for treating senility, enhancing memory or treating amnesia, the compounds utilized in the pharmaceutical method of this invention are administered at the initial dosage of about 5 mg to about 20 mg per kilogram daily. A daily dose range of about 10 mg to about 15 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following non-limiting examples illustrate the inventor's preferred methods for preparing the compounds of the invention.

EXAMPLE 1

2-Propanaminium, N-methyl-N-(1-methylethyl)-N-[2-[[(2-oxo-1-pyrrolidinyl)acetyl]amino]ethyl-,iodide N-[2-[bis(methylethyl)amino]ethyl]-2-oxo-1-pyrrolidineacetamide[a], 42 g (0.146 m) is dissolved in 100 ml acetonitrile; to the solution is added methyl iodide, 25 g (0.17 m) and the reaction mixture is allowed to stand at room temperature overnight. Addition of just enough ethyl ether to achieve dilution without phase separation causes the methiodide to crystallize slowly. The product 2-propanaminium, N-methyl-N-(1-methylethyl)-N-[2-[[(2-oxo-1-pyrrolidinyl)-acetyl]amino]ethyl]-,iodide is collected by filtration and has m.p. 189°–90° C. Recrystallization is from isopropanolacetonitrile, m.p. 191°–2° C.

[a] Described in U.S. Pat. No. 4,145,347 as Example 25.

EXAMPLE 2

2-Propanaminium, N-methyl-N-(1-methylethyl)-N-[2-[[(2-oxo-1-pyrrolidinyl)acetyl]amino]ethyl]-,chloride The quaternary iodide from Example 1, 38 g (0.1 m) is dissolved in 400 ml water and the solution is passed slowly thru an ion exchange resin (Dowex 1-X$_2$ chloride form), 400 ml in a 2 cm diameter column. The eluate and the subsequent 400 ml wash are combined and evaporated in vacuo to leave a residue which is crystallized from the acetonitrile-ether solvent system. The product 2-propanaminium, N-methyl-N-(1-methylethyl)-N-[2-[[(2-oxo-1-pyrrolidinyl)acetyl]amino]ethyl]-,chloride melts at 141°–3° C.

EXAMPLE 3

Piperidinium, 1-methyl-1-[2-[[(2-oxo-1-pyrrolidinyl)acetyl]amino]ethyl]-,iodide

2-Oxo-N-[2-(1-piperidinyl)ethyl]-1-pyrrolidineacetamide[b], 12 g (0.05 m) is reacted with methyl iodide, 10 g (0.07 m) in 30 ml acetonitrile according to the procedure described in Example 1. There is obtained piperidinium, 1-methyl-1-[2-[[(2-oxo-1-pyrrolidinyl)-acetyl]amino]ethyl]-,iodide with m.p. 165°–7° C.

[b] Described in U.S. Pat. No. 4,145,347 as Example 4.

EXAMPLE 4

Ethanaminium, N,N,N,-trimethyl-2-[[(2-oxo-1-pyrrolidinyl)acetyl]amino]-,iodide

N-[2-(dimethylamino)ethyl]-2-oxo-1-pyrrolidineacetamide[c], 13 g (0.06 m) is reacted with methyl iodide 10 g (0.07 m) in acetonitrile following the procedure of Example 1. The product, ethanaminium, N,N,N,-trimethyl-2-[[(2-oxo-1-pyrrolidinyl)acetyl]amino]-,iodide, melts at 170°–1° C.

[c] Example 23 of U.S. Pat. No. 4,145,347.

EXAMPLE 5

Piperidinium,
1-ethyl-1-[2-[[(2-oxo-1-pyrrlidinyl)acetyl]amino]ethyl]-,iodide

Same procedure as Example 3 except that ethyl iodide, 11 g (0.07 m) was used instead of methyl iodide. The product piperidinium, 1-ethyl-1-[2-[[(2-oxo-1-pyrrolidinyl)acetyl]amino]ethyl]-,iodide melts at 120°-2° C.

EXAMPLE 6

Ethanaminium, N,N,1-trimethyl-N-[2-[[(2-oxo-1-pyrrolidinyl)acetyl]amino]ethyl]-,iodide N-[2-[methyl(1-methylethyl)amino]ethyl]-2-oxo-1-pyrrolidine acetamide[d], 10 g (0.04 m) is reacted with methyliodide, 7.5 g (0.05 m) according to procedure of Example 1. The product ethanaminium, N,N, 1-trimethyl-N-[2-[[(2-oxo-1-pyrrolidinyl)acetyl]amino]ethyl]-, iodide melts at 129°-32° C.

[d] Example 24 of U.S. Pat. No. 4,145,347

EXAMPLE 7

Piperidinium,1,2,6-trimethyl-1-[2-[[(2-oxo-1-pyrrolidinyl)acetyl]amino]ethyl]-, iodide N-[2-(2,6-dimethyl-1-piperidinyl)ethyl]-2-oxo-1-pyrrolidine-acetamide[e], 6.4 g (0.022 m) is reacted with methyl iodide, 5.5 g (0.035 m) following the procedure of Example 1. The product piperidinium,1,2,6-trimethyl-1-[2-[[(2-oxo-1-pyrrolidinyl)acetyl]amino]ethyl]-, iodide has m.p. 192°-3° C.

[e] Example 1 of U.S. Pat. No. 4,145,347.

EXAMPLE 8

1-Propanaminium,N,N-dimethyl-N-[2-[[(2-oxo-1-pyrrolidinyl)acetyl]amino]ethyl]-,iodide Same as Example 4 except that n-propyl iodide is used instead of methyl iodide. The product 1-propanaminium, N,N-dimethyl-N-[2-[[(2-oxo-1-pyrrolidinyl)acetyl]amino]ethyl]-,iodide has m.p. 70° C.

EXAMPLE 9

1-Propanaminium,N,N,N-trimethyl-[3-[[(2-oxo-1-pyrrolidinyl)acetyl]amino]ethyl]-,chloride N-[3-dimethylamino)propyl]-2-oxo-1-pyrrolidineacetamine[f], 11.3 g (0.05 m) is reacted with methyliodide, 8.5 g (0.06 m) following procedure of Example 1 to give the product as iodide, m.p. 210°-2° C. Using the procedure described in Example 2, 10 g of this iodide is converted to 1-propanaminium,N,N,N-trimethyl-[3-[[(2-oxo-1-pyrrolidinyl)acetyl]amino]ethyl]-,chloride; m.p. 204°-5° C.

[f] Example 2 of U.S. Pat. No. 4,145,347.

I claim:

1. A compound having the structural formula:

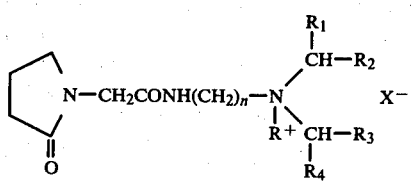

wherein R is alkyl of from 1 to 3 carbon atoms, $R_1$ and $R_4$ may be the same or different and are hydrogen or methyl; $R_2$ and $R_3$ may be the same or different and are hydrogen, alkyl of from 1 to 3 carbon atoms or when taken together can complete a pyrrolidine, piperidine, morpholine or piperazine ring; n is an integer of from 1 to 3; $X^-$ is a pharmaceutically acceptable anion; with the proviso that when R is n-$C_3H_7$, n is 2 and $X^-$ is I; then $R_1$-$R_4$ may not all be hydrogen.

2. The compounds defined in claim 1 wherein $X^-$ is $Cl^-$.

3. The compound defined in claim 1 which is 2-propanaminium, N-methyl-N-(1-methylethyl)-N-[2-[[(2-oxo-1-pyrrolidinyl)acetyl]amino]ethyl]-,iodide.

4. The compound defined in claim 1 which is 2-propanaminium, N-methyl-N-(1-methylethyl)-N-[2-[[(2-oxo-1-pyrrolidinyl)acetyl]amino]ethyl]-,chloride.

5. The compound defined in claim 1 which is piperidinium, 1-methyl-1-[2-[[(2-oxo-1-pyrrolidinyl)acetyl]amino]ethyl]-,iodide.

6. The compound defined in claim 1 which is ethanaminium, N,N,N,-trimethyl-2-[[(2-oxo-1-pyrrolidinyl)acetyl]amino]-,iodide.

7. The compound defined in claim 1 which is piperidinium, 1-ethyl-1-[2-[[(2-oxo-1-pyrrolidinyl)acetyl]amino]ethyl]-,iodide.

8. The compound defined in claim 1 which is ethanaminium, N,N, 1-trimethyl-N-[2-[[(2-oxo-1-pyrrolidinyl)acetyl]amino]ethyl]-,iodide.

9. The compound defined in claim 1 which is piperidinium,1,2,6-trimethyl-1-[2-[[(2-oxo-1-pyrrolidinyl)acetyl]amino]ethyl]-,iodide.

10. The compound defined in claim 1 which is 1-propanaminium,N,N,N-trimethyl-[3-[[(2-oxo-1-pyrrolidinyl)acetyl]amino]ethyl]-,chloride.

11. A pharmaceutical composition useful for the treatment of senility, enhancing memory or reversing amnesia in a mammal which comprises an effective amount of a compound as defined in claim 1, or mixtures thereof; in combination with a pharmaceutically acceptable carrier.

12. A method for treating senility, of enhancing memory or of reversing amnesia in a mammal which comprises administering to a mammal in need of thereof an effective amount of the pharmaceutical composition as defined in claim 11.

* * * * *